(12) United States Patent
FitzGerald et al.

(10) Patent No.: US 7,824,695 B1
(45) Date of Patent: Nov. 2, 2010

(54) DELIVERY OF PROTEINS ACROSS POLAR EPITHELIAL CELL LAYERS

(75) Inventors: David J. FitzGerald, Rockville, MD (US); Randall J. Mrsny, Los Altos Hills, CA (US); Marian McKee, Great Falls, VA (US); Ann Daugherty, Los Altos Hills, CA (US)

(73) Assignees: The United States of America as represented by the Department of Health and Human Services, Washington, DC (US); Genentech, Inc., South San Francisco, CA (US)

( * ) Notice: Subject to any disclaimer, the term of this patent is extended or adjusted under 35 U.S.C. 154(b) by 1927 days.

(21) Appl. No.: 10/110,880

(22) PCT Filed: Oct. 18, 2000

(86) PCT No.: PCT/US00/29080

§ 371 (c)(1),
(2), (4) Date: Apr. 16, 2002

(87) PCT Pub. No.: WO01/30392

PCT Pub. Date: May 3, 2001

Related U.S. Application Data (60) Provisional application No. 60/160,923, filed on Oct. 22, 1999.

(51) Int. Cl.
| | |
|---|---|
| A61K 39/108 | (2006.01) |
| A61K 39/38 | (2006.01) |
| A61K 38/00 | (2006.01) |
| G01N 1/00 | (2006.01) |
| G01N 33/554 | (2006.01) |
| C07K 1/00 | (2006.01) |
| C07H 21/02 | (2006.01) |

(52) U.S. Cl. ............... 424/260.1; 424/184.1; 435/174; 436/519; 530/324; 530/350; 536/23.1

(58) Field of Classification Search ............... 424/85.2, 424/93.47, 130.1, 134.1, 170.1, 190.1; 435/6, 435/7.2, 69.4
See application file for complete search history.

(56) References Cited

U.S. PATENT DOCUMENTS

| 5,696,077 A | * | 12/1997 | Johnson et al. ............... 514/2 |
| 2002/0106370 A1 | | 8/2002 | Cardy |
| 2004/0071731 A1 | | 4/2004 | Fitzgerald |
| 2005/0079171 A1 | | 4/2005 | Fitzgerald et al. |

FOREIGN PATENT DOCUMENTS

| WO | WO 86/06635 A1 | | 11/1986 |
| WO | WO 95/07297 A1 | | 3/1995 |
| WO | WO 98/20135 | * | 5/1998 |
| WO | WO 9820135 | * | 5/1998 |
| WO | WO 98/42876 | * | 10/1998 |
| WO | WO 98/42876 A1 | | 10/1998 |
| WO | WO 00/46246 A1 | | 8/2000 |
| WO | WO 01/30392 A2 | | 5/2001 |
| WO | WO 01/31020 A1 | | 5/2001 |

OTHER PUBLICATIONS

Mrsny et al (Vaccine 17 Mar. 1999, p. 1425-1433).*
Fitzgerald et al (The Journal of Biological Chemistry, vol. 272, No. 16, Apr. 17, 1998, p. 9951-9958).*
Andreasen, P.A. et al., "Receptor-mediated endocytosis of plasminogen activators and activator/inhibitor complexes." *FEBS Letters*, vol. 338, No. 3; pp. 239-245 (1994).
Cavallaro, U. et al., "Targeting plant toxins to the urokinase and α-2-macroglobulin receptors." *Semin. Cancer Biol.*, vol. 6, No. 5; pp. 269-278 (1995).
Daugherty, A.L. et al., "Epithelial application of *Pseudomonas aeruginosa* exotoxin A results in a selective targeting to cells in the liver, spleen and lymph node." *J. Controlled Release*, vol. 65, Nos. 1-2; pp. 297-302 (2000).
Fitzgerald, D.J., et al., "Characterization of V3 loop-*Pseudonomas* exotoxin chimeras. Candidate vaccines for human immunodeficiency virus-1." *J. Biol. Chem.*, vol. 273, No. 16; pp. 9951-9958 (1998).
Herz J. and D.K Strickland, "LRP: a multifunctional scavenger and signaling receptor." *J Clin Invest.*, vol. 108, No. 6; pp. 779-784. (2001).
Maziere, J.C. et al., "Processing and characterization of the low density lipoprotein receptor in the human colonic carcinoma cell subclone HT29-18: a potential pathway for delivering therapeutic drugs and genes." *Biosci. Rep.*, vol. 12, No. 6; pp. 483-494 (1992).
Melman, L. et al., "High affinity binding of receptor-associated protein to heparin and low density lipoprotein receptor-related protein requires similar basic amino acid sequence motifs." *J. Biol. Chem.*, vol. 276, No. 31; pp. 29338-29346 (2001).
Mrsny R.J. et al.. "Mucosal administration of a chimera composed of *Pseudomonas* exotoxin and the gp120 V3 loop sequence of HIV-1 induces both salivary and serum antibody responses." *Vaccine*, vol. 17, Nos. 11-12; pp. 1425-1433 (1999).
Versluis, A.J. et al., "Stable incorporation of a lipophilic daunorubicin prodrug into apoliproteln E-exposing liposomes induces uptake of prodrug via low-density lipoprotein receptor in vivo." *J. Pharmacol. Experiment Therap.*, vol. 289, No. 1; pp. 1-7 (1999).
Zdanovsky, A.G. et al., "Targeting *Pseudomonas* and diphtheria toxins to the alpha-2-macroglobulin receptor via RAP-toxin and PAI-I-toxin fusions." *Prot. Engin.*, vol. 8, No. Suppl., pp. 123 (1995).
U.S. Appl. No. 09/462,682, filed Apr. 28, 2000, Fitzgerald.

* cited by examiner

*Primary Examiner*—Vanessa L. Ford
(74) *Attorney, Agent, or Firm*—Townsend and Townsend and Crew LLP (57) ABSTRACT

This invention provides bioactive conjugates. The bioactive conjugates include: (1) a cell recognition moiety that binds to $\alpha_2$ macroglobulin receptor α2-MR and (2) a bioactive moiety which: (a) has a biological activity, (b) does not function solely as an immunogen to invoke an immune response and (c) does not have ADP ribosylating activity. The bioactive conjugates of this invention are useful in methods of transporting the bioactive moiety across a polar epithelial membrane. Thus, this invention provides methods for parenteral administration of proteins without injection.

30 Claims, 2 Drawing Sheets

DELIVERY OF PROTEINS ACROSS POLAR EPITHELIAL CELL LAYERS

CROSS-REFERENCES TO RELATED APPLICATIONS

This application claims priority to provisional application U.S. Ser. No. 60/160,923 filed Oct. 22, 1999, the disclosure of which is herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This invention is directed to the fields of molecular biology and medicine.

Recombinant DNA technology has made it possible to produce large amounts of highly purified proteins. Many of these proteins are now in use as pharmaceuticals. Recombinantly produced pharmaceutical proteins include, for example, insulin, erythropoietin, human growth hormone and β-interferon.

Pharmaceutical proteins which need to gain systemic access cannot be administered enterally because the enzymes of the digestive system degrade the proteins before they gain access. Therefore, pharmaceutical proteins generally are administered by injection. Diseases that require repeated administration of a protein over a long period of time, such as diabetes, can require daily injection. Of course, frequent injections are not pleasant for the patient and may not be the best method of administration. Therefore, means to deliver proteins without injection would provide an advantage.

Various proteins are known to gain access to the system by traversing mucosal surfaces. For example, van Deurs et al. (European J. Cell Biol., 51:96 (1990)) showed that ricin crosses the epithelium by transcytosis. EP 0 222 835 B1 (Russell-Jones et al. May 25, 1987) discusses the use of carrier molecules that specifically interact with the mucosal epithelium, including various toxins, for the oral delivery of immunogens for inducing cell-mediated immunity.

*Pseudomonas* exotoxin A (PE) is a toxic protein produced by the bacterium, *Pseudomonas aeruginosa*. In its native form, the protein binds to the α2-macroglobulin receptor ("α2-MR") which is found on the surface of many cells. The molecule comprises four domains. Domain Ia binds α2-MR. Domain II is responsible for endocytosis of the molecule into the cell. Domain Ib has no identified function. Domain III is responsible for toxicity (by mediating inactivation of protein synthesis) and acts to retain the toxin in the endoplasmic reticulum. PE has been extensively re-engineered to give the molecule new properties. For example, domain Ia has been replaced with proteins that bind to specific target receptors. Targeting proteins also have been engineered into domain III to provide a binding capability. Such constructs have found use as immunotoxins. Domain III has been modified to eliminate the ADP ribosylation activity. Domain II has been shortened while retaining translocation ability. Thus, the domains of PE act as relatively independent functional units which can be exchanged for other functional units and that can be extensively engineered within themselves. See, for example, U.S. Pat. No. 5,863,745 (FitzGerald et al.); U.S. Pat. No. 5,854,044 (Pastan et al.); U.S. Pat. No. 5,705,163 (Pastan et al.); U.S. Pat. No. 5,705,156 (Pastan et al.); U.S. Pat. No. 5,696,237 (FitzGerald et al.); U.S. Pat. No. 5,602,095 (Pastan et al.); U.S. Pat. No. 5,458,878 (Pastan et al.); U.S. Pat. No. 5,082,927 (Pastan et al.); U.S. Pat. No. 4,892,827 (Pastan et al.); Y. Reiter et al. *Nature Biotechnology* (1996) 14:1239 and U. Brinkmann and I. Pastan, *Biochim. et Biophys. Acta* (1994) 1198:27.

SUMMARY OF THE INVENTION

Molecules that bind α2 macroglobulin receptor, when applied to the apical surface of a polarized epithelial cell layer, are able to traverse through the basal side of the membrane into the sub-epithelial space. This invention takes advantage of that fact by using molecules that bind the α2 macroglobulin receptor as carriers to deliver proteins and molecules bound to them across the epithelial surface without resorting to injection of the protein. This use for such binding molecules is unexpected, because one could not have predicted that proteins coupled to them would retain activity upon transit. Thus, this invention provides methods for parenteral administration of a protein by transmucosal delivery and without injection. This invention finds use in the administration of protein pharmaceuticals that are subject to repeated injection, such as insulin, interferons, growth hormone and erythropoietin.

In another aspect this invention provides a bioactive conjugate comprising: (1) a cell recognition moiety that binds to $\alpha_2$ macroglobulin receptor (α2-MR) and (2) a bioactive moiety which: (a) has a biological activity selected from receptor binding, cytokine activity, enzymatic activity, hormonal activity, interleukin activity, neurotransmitter activity, regulation of transcription or translation and affinity for a bioorganic molecule, (b) does not function solely as an immunogen to invoke an immune response and (c) does not have ADP ribosylating activity.

In one embodiment, the epithelial cell layer is a membrane cultured in vitro. In another embodiment the epithelial cell layer is a mucosal surface of a mammalian subject.

In other embodiments the cell recognition moiety comprises an antibody that binds α2-microglobulin, comprises a portion of *Pseudomonas* exotoxin A (PE) domain Ia sufficient to bind α2-microglobulin or comprises *Pseudomonas* exotoxin A (PE) domain Ia and the conjugate further comprises domain II of PE. In another embodiment the conjugate is a PE conjugate comprising: (a) *Pseudomonas* exotoxin A (PE) domain Ia; (b) a PE moiety sufficient to effect translocation from the apical surface to the basal surface of the polar epithelial cell layer, said PE moiety comprising PE domain II, at least a portion of PE domain III, wherein the portion does not possess ribosylation activity, and, optionally, PE domain Ib; and wherein the bioactive moiety comprises a polypeptide.

In other embodiments the mucosal surface is a mucosal surface of the respiratory system, gastrointestinal system or reproductive system.

In other embodiments the bioactive moiety comprises a polypeptide which comprises an antibody, a lectin, a DNA binding protein, a lipid binding protein, a ligand for a cell surface receptor, an enzyme, insulin, an interferon, a growth hormone or an erythropoietin. In another embodiment the bioactive moiety comprises a polypeptide ligand bound to a second polypeptide, a carbohydrate, a lipid or a nucleic acid.

In another embodiment the bioactive moiety comprises a polypeptide and the conjugate comprises a fusion protein wherein the cell recognition moiety is fused to the polypeptide. In another embodiment, the fusion protein comprises a cleavage site recognized by a protease, wherein cleavage releases the bioactive moiety from the fusion protein.

In one aspect this invention provides a method for transporting a bioactive moiety across a polar epithelial cell layer comprising administering to the apical surface of the cell layer a bioactive conjugate of this invention.

In another aspect this invention provides a pharmaceutical composition comprising a pharmaceutically acceptable carrier and a bioactive conjugate of this invention, wherein the pharmaceutical composition is formulated for topical administration.

In another aspect this invention provides a nucleic acid comprising a nucleotide sequence that encodes a fusion protein conjugate wherein the fusion protein comprises: (1) a cell recognition moiety that binds to $\alpha_2$ macroglobulin receptor ($\alpha$2-MR) fused to (2) a bioactive moiety having an activity to alter the expression or activity of a gene or gene product, wherein the bioactive moiety: (a) has a biological activity selected from receptor binding, cytokine activity, enzymatic activity, hormonal activity, interleukin activity, neurotransmitter activity, regulation of transcription or translation and affinity for a bioorganic molecule, (b) does not function solely as an immunogen to invoke an immune response and (c) does not have ADP ribosylating activity.

BRIEF DESCRIPTION OF THE DRAWINGS

FIG. 2 is a diagram of PE structure. The amino acid position based on SEQ ID NO:2 is indicated. Domain 1a extends from amino acids 1-252. Domain II extends from amino acids 253-364. It includes a cysteine-cysteine loop formed by cysteines at amino acids 265-287. Furin cleaves within the cysteine-cysteine loop between amino acids 279 and 280. A fragment of PE beginning with amino acid 280 translocates to the cytosol. Constructs in which amino acids 345-364 are eliminated also translocate. Domain 1b spans amino acids 365-399. It contains a cysteine-cysteine loop formed by cysteines at amino acids 372 and 379. The domain can be eliminated entirely. Domain III spans amino acids 400-613. Deletion of amino acid 553 eliminates ADP ribosylation activity. The endoplasmic reticulum sequence, REDLK (amino acids 600-605 of SEQ ID NO:2) is located at the carboxy-terminus of the molecule, from amino acid 609-613.

DETAILED DESCRIPTION OF THE INVENTION

I. Definitions

Figure 1:
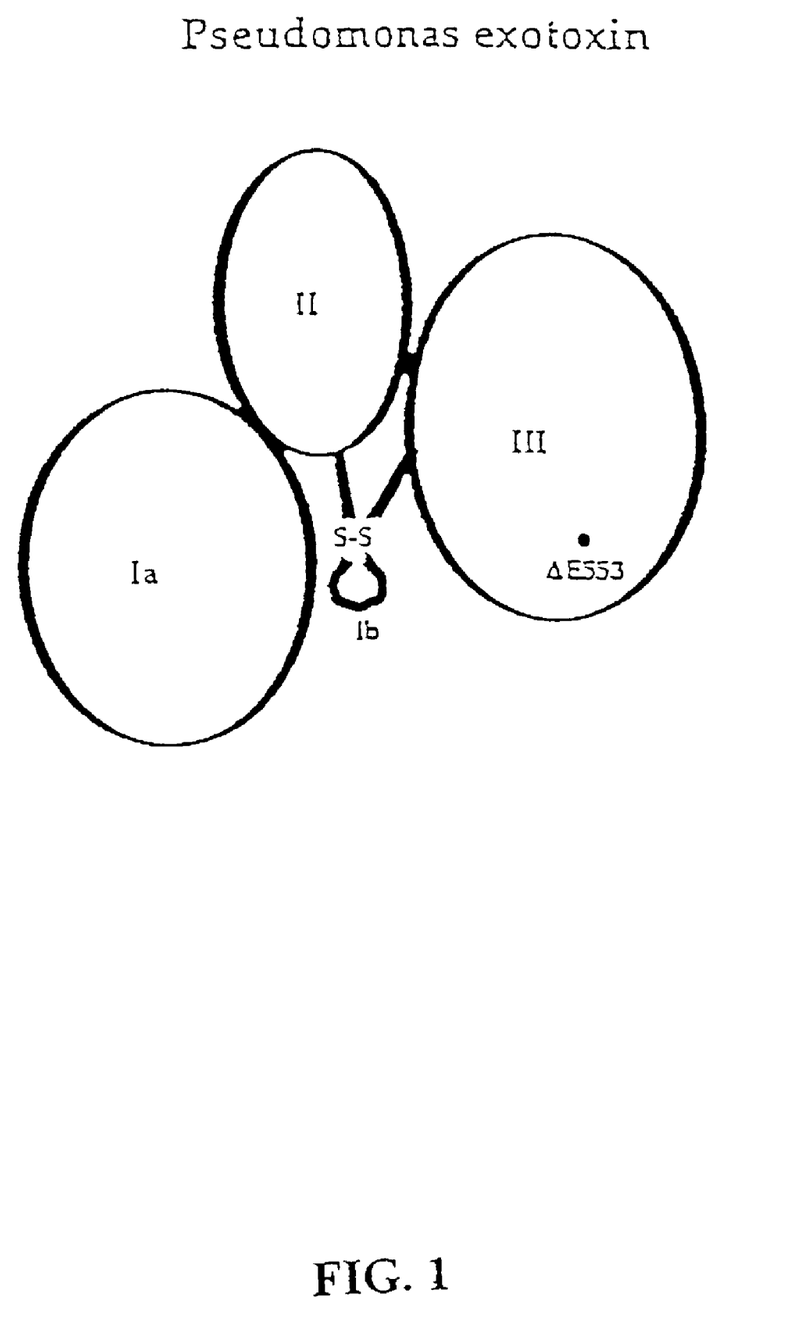
FIG. 1 is a schematic of *Pseudomonas* exotoxin A ("PE") structure.
Figure 2:
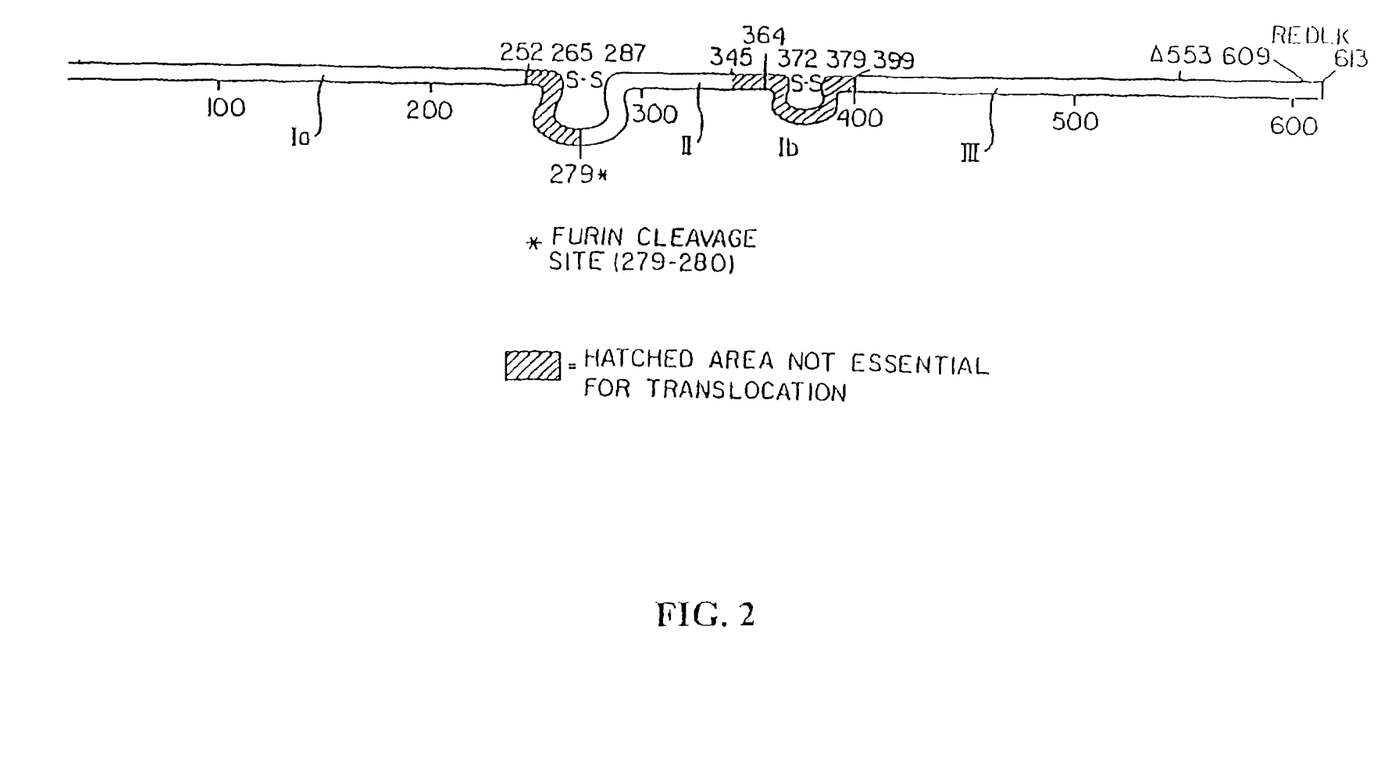

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). As used herein, the following terms have the meanings ascribed to them unless specified otherwise.

"Nucleic acid" refers to a polymer composed of nucleotide units (ribonucleotides, deoxyribonucleotides, related naturally occurring structural variants, and synthetic non-naturally occurring analogs thereof) linked via phosphodiester bonds or other synthetic bond. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the "transcription direction." The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. An amplified or assembled recombinant nucleic acid may be included in a suitable vector, and the vector can be used to transform a suitable host cell. A host cell that comprises the recombinant nucleic acid is referred to as a "recombinant host cell." The gene is then expressed in the recombinant host cell to produce, e.g., a "recombinant polypeptide." A recombinant nucleic acid may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression cassette" refers to a recombinant nucleic acid construct comprising an expression control sequence operatively linked to an expressible nucleotide sequence. An expression cassette generally comprises sufficient cis-acting elements for expression; other elements for expression can be supplied by the host cell or in vitro expression system.

"Expression vector" refers to a vector comprising an expression cassette. Expression vectors include all those known in the art, such as cosmids, plasmids (e.g., naked or contained in liposomes) and viruses that incorporate the expression cassette.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

"Fusion protein" refers to a polypeptide formed by the joining of two or more polypeptides through a peptide bond formed by the amino terminus of one polypeptide and the carboxyl terminus of the other polypeptide. A fusion protein may is typically expressed as a single polypeptide from a nucleic acid sequence encoding the single contiguous fusion protein. However, a fusion protein can also be formed by the chemical coupling of the constituent polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variants" also refer to cDNAs derived from mRNA transcripts of genetic allelic variants, as well as the proteins encoded by them.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984).

Another example of algorithms that are suitable for determining percent sequence identity and sequence similarity are the BLAST and the BLAST 2.0 algorithms, which are described in Altschul et al., *J. Mol. Biol.* 215: 403-410 (1990) and Altschul et al., *Nucleic Acids Res.* 25: 3389-3402 (1977)). Software for performing BLAST analyses is publicly available through the National Center for Biotechnology Information of the U.S. National Institutes for Health. The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89: 10915 (1989)).

"Stringent hybridization conditions" refers to 50% formamide, 5×SSC and 1% SDS incubated at 42° C. or 5×SSC and 1% SDS incubated at 65° C., with a wash in 0.2×SSC and 0.1% SDS at 65° C.

A "ligand" is a compound that specifically binds to a target molecule.

A "receptor" is compound that specifically binds to a ligand.

"Antibody" refers to a polypeptide ligand comprising at least a light chain or heavy chain immunoglobulin variable region which specifically binds and recognizes an epitope (e.g., an antigen). This includes intact immunoglobulins and the variants and portions of them well known in the art such as, Fab' fragments, F(ab)'2 fragments, and scFv proteins. An scFv protein is a fusion protein in which a light chain variable region and a heavy chain variable region bound by a linker. Natural immunoglobulins are encoded by immunoglobulin genes. These include the kappa and lambda light chain constant region genes, the alpha, gamma, delta, epsilon and mu heavy chain constant region genes, and the myriad immunoglobulin variable region genes. The term "antibody" includes polyclonal antibodies, monoclonal antibodies, chimeric antibodies and humanized antibodies, produced by immunization, from hybridomas, or recombinantly.

A ligand or a receptor "specifically binds to" an analyte when the ligand or receptor functions in a binding reaction which is determinative of the presence of the analyte in a sample of heterogeneous compounds. Thus, the ligand or receptor binds preferentially to a particular analyte and does not bind in a significant amount to other compounds present in the sample. For example, a polynucleotide specifically binds to an analyte polynucleotide comprising a complementary sequence and an antibody specifically binds under immunoassay conditions to an antigen analyte bearing an epitope against which the antibody was raised.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition.

"Linker" refers to a molecule that joins two other molecules, either covalently, or through ionic, van der Waals or hydrogen bonds.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in REMINGTON'S PHARMACEUTICAL SCIENCES, 19th Ed. (Mack Publishing Co., Easton, 1995). Preferred pharmaceutical carriers depend upon the intended mode of administration of the active agent. The conjugates of this invention are delivered to mucosal surfaces. A "pharmaceutically acceptable salt" is a salt that can be formulated into a compound for pharmaceutical use including, e.g., metal salts (sodium, potassium, magnesium, calcium, etc.) and salts of ammonia or organic amines.

A "subject" of diagnosis or treatment is a human or non-human mammal. Non-human mammals subject to diagnosis or treatment include, for example, primates, ungulates, canines and felines. The subject can be a farm animal such a cattle, horse, sheep, pig or goat.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

"Diagnostic" means identifying the presence or nature of a pathologic condition. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis.

"Prognostic" means predicting the probable development (e.g., severity) of a pathologic condition.

"Bioactive moiety" refers to a bioorganic molecule which (a) has a biological activity selected from receptor binding, cytokine activity, enzymatic activity, hormonal activity, interleukin activity, neurotransmitter activity, regulation of transcription or translation and affinity for another bioorganic molecule (e.g., an immunoglobulin), (b) does not function solely as an immunogen to invoke an immune response and (c) does not have ADP ribosylating activity.

"Bioorganic molecule" refers to an organic molecule of the class typically made by living organisms. This includes, for example, molecules comprising nucleotides, amino acids, sugars, fatty acids, steroids, nucleic acids, polypeptides, carbohydrates, lipids, combinations of these (e.g., glycoproteins, ribonucleoproteins, lipoproteins).

"*Pseudomonas* exotoxin A" or "PE" is secreted by Ps aeruginosa as a 67 kD protein composed of three prominent globular domains (Ia, II, and III) and one small subdomain (Ib) connecting domains II and III. (A. S. Allured et. al. (1986) *Proc. Natl. Acad. Sci.* 83:1320-1324.) Domain Ia of PE mediates cell binding. In nature, domain Ia binds to the low density lipoprotein receptor-related protein ("LRP"), also known as the α2-macroglobulin receptor ("α2-MR"). (M. Z. Kounnas et al. (1992) *J. Biol. Chem.* 267:12420-23.) It spans amino acids 1-252. Domain II mediates translocation to the cytosol. It spans amino acids 253-364. Domain Ib has no known function. It spans amino acids 365-399. Domain III is responsible for cytotoxicity and includes an endoplasmic reticulum retention sequence. It mediates ADP ribosylation of elongation factor 2, which inactivates protein synthesis. It spans amino acids 400-613. PE is "non-toxic" if it lacks EF2 ADP ribosylation activity. Deleting amino acid E553 ("ΔE553") from domain III detoxifies the molecule. PE having the mutation ΔE553 is referred to herein as "PE ΔE553." Allelic forms of PE are included in this definition. See, e.g., M. L. Vasil et al., (1986) *Infect. Immunol.*, 52:538-48. The nucleotide sequence (SEQ ID NO:1) and deduced amino acid sequence (SEQ ID NO:2) of *Pseudomonas* exotoxin A are:

```
GCC GAA GAA GCT TTC GAC CTC TGG AAC GAA TGC GCC AAA GCC TGC GTG      48
Ala Glu Glu Ala Phe Asp Leu Trp Asn Glu Cys Ala Lys Ala Cys Val
 1               5                  10                  15

CTC GAC CTC AAG GAC GGC GTG CGT TCC AGC CGC ATG AGC GTC GAC CCG      96
Leu Asp Leu Lys Asp Gly Val Arg Ser Ser Arg Met Ser Val Asp Pro
             20                  25                  30

GCC ATC GCC GAC ACC AAC GGC CAG GGC GTG CTG CAC TAC TCC ATG GTC     144
Ala Ile Ala Asp Thr Asn Gly Gln Gly Val Leu His Tyr Ser Met Val
                 35                  40                  45

CTG GAG GGC GGC AAC GAC GCG CTC AAG CTG GCC ATC GAC AAC GCC CTC     192
Leu Glu Gly Gly Asn Asp Ala Leu Lys Leu Ala Ile Asp Asn Ala Leu
         50                  55                  60

AGC ATC ACC AGC GAC GGC CTG ACC ATC CGC CTC GAA GGC GGC GTC GAG     240
Ser Ile Thr Ser Asp Gly Leu Thr Ile Arg Leu Glu Gly Gly Val Glu
 65                  70                  75                  80
```

-continued

```
CCG AAC AAG CCG GTG CGC TAC AGC TAC ACG CGC CAG GCG CGC GGC AGT         288
Pro Asn Lys Pro Val Arg Tyr Ser Tyr Thr Arg Gln Ala Arg Gly Ser
             85                  90                  95

TGG TCG CTG AAC TGG CTG GTA CCG ATC GGC CAC GAG AAG CCC TCG AAC         336
Trp Ser Leu Asn Trp Leu Val Pro Ile Gly His Glu Lys Pro Ser Asn
            100                 105                 110

ATC AAG GTG TTC ATC CAC GAA CTG AAC GCC GGC AAC CAG CTC AGC CAC         384
Ile Lys Val Phe Ile His Glu Leu Asn Ala Gly Asn Gln Leu Ser His
            115                 120                 125

ATG TCG CCG ATC TAC ACC ATC GAG ATG GGC GAC GAG TTG CTG GCG AAG         432
Met Ser Pro Ile Tyr Thr Ile Glu Met Gly Asp Glu Leu Leu Ala Lys
130                 135                 140

CTG GCG CGC GAT GCC ACC TTC TTC GTC AGG GCG CAC GAG AGC AAC GAG         480
Leu Ala Arg Asp Ala Thr Phe Phe Val Arg Ala His Glu Ser Asn Glu
145                 150                 155                 160

ATG CAG CCG ACG CTC CCC ATC AGC CAT GCC GGG GTC AGC GTG GTC ATG         528
Met Gln Pro Thr Leu Pro Ile Ser His Ala Gly Val Ser Val Val Met
                165                 170                 175

GCC CAG ACC CAG CCG CGC CGG GAA AAG CGC TGG AGC GAA TGG GCC AGC         576
Ala Gln Thr Gln Pro Arg Arg Glu Lys Arg Trp Ser Glu Trp Ala Ser
                180                 185                 190

GGC AAG GTG TTG TGC CTG CTC GAC CCG CTG GAC GGG GTC TAC AAC TAC         624
Gly Lys Val Leu Cys Leu Leu Asp Pro Leu Asp Gly Val Tyr Asn Tyr
            195                 200                 205

CTC GCC CAG CAA CGC TGC AAC CTC GAC GAT ACC TGG GAA GGC AAG ATC         672
Leu Ala Gln Gln Arg Cys Asn Leu Asp Asp Thr Trp Glu Gly Lys Ile
210                 215                 220

TAC CGG GTG CTC GCC GGC AAC CCG GCG AAG CAT GAC CTG GAC ATC AAA         720
Tyr Arg Val Leu Ala Gly Asn Pro Ala Lys His Asp Leu Asp Ile Lys
225                 230                 235                 240

CCC ACG CTG ATC AGT CAT CGC CTG CAC TTT CCC GAG GGC GGC AGC CTG         768
Pro Thr Val Ile Ser His Arg Leu His Phe Pro Glu Gly Gly Ser Leu
                245                 250                 255

GCC GCG CTG ACC GCG CAC CAG GCT TGC CAC CTG CCG CTG GAG ACT TTC         816
Ala Ala Leu Thr Ala His Gln Ala Cys His Leu Pro Leu Glu Thr Phe
                260                 265                 270

ACC CGT CAT CGC CAG CCG CGC GGC TGG GAA CAA CTG GAG CAG TGC GGC         864
Thr Arg His Arg Gln Pro Arg Gly Trp Glu Gln Leu Glu Gln Cys Gly
            275                 280                 285

TAT CCG GTG CAG CGG CTG GTC GCC CTC TAC CTG GCG GCG CGG CTG TCG         912
Tyr Pro Val Gln Arg Leu Val Ala Leu Tyr Leu Ala Ala Arg Leu Ser
290                 295                 300

TGG AAC CAG GTC GAC CAG GTG ATC CGC AAC GCC CTG GCC AGC CCC GGC         960
Trp Asn Gln Val Asp Gln Val Ile Arg Asn Ala Leu Ala Ser Pro Gly
305                 310                 315                 320

AGC GGC GGC GAC CTG GGC GAA GCG ATC CGC GAG CAG CCG GAG CAG GCC        1008
Ser Gly Gly Asp Leu Gly Glu Ala Ile Arg Glu Gln Pro Glu Gln Ala
                325                 330                 335

CGT CTG GCC CTG ACC CTG GCC GCC GCC GAG AGC GAG CGC TTC GTC CGG        1056
Arg Leu Ala Leu Thr Leu Ala Ala Ala Glu Ser Glu Arg Phe Val Arg
                340                 345                 350

CAG GGC ACC GGC AAC GAC GAG GCC GGC GCG GCC AAC GGC GAC GTG GTG        1104
Gln Gly Thr Gly Asn Asp Glu Ala Gly Ala Ala Asn Gly Asp Val Val
            355                 360                 365

AGC CTG ACC TGC CCG GTC GCC GCC GGT GAA TGC GCG GGC CCG GCG GAC        1152
Ser Leu Thr Cys Pro Val Ala Ala Gly Glu Cys Ala Gly Pro Ala Asp
370                 375                 380

AGC GGC GAC GCC CTG CTG GAG CGC AAC TAT CCC ACT GGC GCG GAG TTC        1200
Ser Gly Asp Ala Leu Leu Glu Arg Asn Tyr Pro Thr Gly Ala Glu Phe
385                 390                 395                 400
```

```
CTC GGC GAC GGC GGC GAC GTC AGC TTC AGC ACC CGC GGC ACG CAG AAC     1248
Leu Gly Asp Gly Gly Asp Val Ser Phe Ser Thr Arg Gly Thr Gln Asn
                405                     410                 415

TGG ACG GTG GAG CGG CTC CTC CAG GCG CAC CGC CAA CTG GAG GAG CGC     1296
Trp Thr Val Glu Arg Leu Leu Gln Ala His Arg Gln Leu Glu Glu Arg
            420                     425                 430

GGC TAT GTG TTC GTC GGC TAC CAC GGC ACC TTC CTC GAA GCG GCG CAA     1344
Gly Tyr Val Phe Val Gly Tyr His Gly Thr Phe Leu Glu Ala Ala Gln
                435                     440                 445

AGC ATC GTC TTC GGC GGG GTG CGC GCG CGC AGC CAG GAC CTC GAC GCG     1392
Ser Ile Val Phe Gly Gly Val Arg Ala Arg Ser Gln Asp Leu Asp Ala
            450                     455                 460

ATC TGG CGC GGT TTC TAT ATC GCC GGC GAT CCG GCG CTG GCC TAC GGC     1440
Ile Trp Arg Gly Phe Tyr ILe Ala Gly Asp Pro Ala Leu Ala Tyr Gly
465                     470                     475             480

TAC GCC CAG GAC CAG GAA CCC GAC GCA CGC GGC CGG ATC CGC AAC GGT     1488
Tyr Ala Gln Asp Gln Glu Pro Asp Ala Arg Gly Arg Ile Arg Asn Gly
                485                     490                 495

GCC CTG CTG CGG GTC TAT GTG CCG CGC TCG AGC CTG CCG GGC TTC TAC     1536
Ala Leu Leu Arg Val Tyr Val Pro Arg Ser Ser Leu Pro Gly Phe Tyr
            500                     505                 510

CGC ACC AGC CTG ACC CTG GCC GCG CCG GAG GCG GCG GGC GAG GTC GAA     1584
Arg Thr Ser Leu Thr Leu Ala Ala Pro Glu Ala Ala Gly Glu Val Glu
                515                     520                 525

CGG CTG ATC GGC CAT CCG CTG CCG CTG CGC CTG GAC GCC ATC ACC GGC     1632
Arg Leu Ile Gly His Pro Leu Pro Leu Arg Leu Asp Ala Ile Thr Gly
            530                     535                 540

CCC GAG GAG GAA GGC GGG CGC CTG GAG ACC ATT CTC GGC TGG CCG CTG     1680
Pro Glu Glu Glu Gly Gly Arg Leu Glu Thr Ile Leu Gly Trp Pro Leu
545                     550                     555             560

GCC GAG CGC ACC GTG GTG ATT CCC TCG GCG ATC CCC ACC GAC CCG CGC     1728
Ala Glu Arg Thr Val Val Ile Pro Ser Ala Ile Pro Thr Asp Pro Arg
                565                     570                 575

AAC GTC GGC GGC GAC CTC GAC CCG TCC AGC ATC CCC GAC AAG GAA CAG     1776
Asn Val Gly Gly Asp Leu Asp Pro Ser Ser Ile Pro Asp Lys Glu Gln
            580                     585                 590

GCG ATC AGC GCC CTG CCG GAC TAC GCC AGC CAG CCC GGC AAA CCG CCG     1824
Ala Ile Ser Ala Leu Pro Asp Tyr Ala Ser Gln Pro Gly Lys Pro Pro
            595                     600                 605

CGC GAG GAC CTG AAG                                                 1839
Arg Glu Asp Leu Lys
            610
```

II. Bioactive Conjugates that Cross Epithelial Membranes

A. Basic Structure

This invention provides bioactive conjugates capable of crossing from an apical surface to a bases surface of an epithelial membrane to which they are applied. The bioactive conjugates of this invention include: (1) a cell recognition moiety and (2) a bioactive moiety. The cell recognition moiety is a polypeptide moiety that functions to bind to a receptor on the apical surface of an epithelial membrane, most preferably $\alpha_2$ macroglobulin receptor ($\alpha$2-MR). In a preferred embodiment, the conjugate comprises a fusion protein in which the cell recognition domain and a polypeptide bioactive moiety are produced as a single polypeptide. However, the conjugate can be prepared by chemically coupling the moieties to each other.

In certain embodiments the conjugates of this invention are "PE conjugates" which further comprise (3) a "PE moiety" that mediates translocation of a conjugate bound to the apical surface of a cell in an epithelial membrane to the cytosol of the cell, on its way to being transported to the basal side of the membrane. In certain embodiments, the bioactive moiety is not positioned within the 1b domain of PE. Native PE or detoxified version of it that have not been altered to contain any other bioactive function are not conjugates of this invention.

B. Cell Recognition Moiety

The conjugates of this invention comprise an amino acid sequence encoding a "cell recognition moiety." The cell recognition moiety functions as a ligand for a cell surface receptor on the apical surface of a polar epithelial cell layer and mediates binding of the conjugate to a cell. The purpose of the moiety is to bind the conjugate to the surface of the membrane, which the first, essential step for translocation to the basal side of the membrane. In a PE conjugate of the invention, the cell recognition moiety preferably is located in the position of domain Ia of PE. However, this domain can be moved out of the normal organizational sequence. More particularly, the cell recognition moiety can be inserted in the location of PE domain III, after about the first 70 amino acids of that domain. Also, the cell recognition moiety can be chemically coupled to the conjugate.

The cell recognition domain can be located in any position that allows it to perform its cell-binding function. In a preferred embodiment, the cell recognition moiety is located in place of domain Ia of PE. It can be attached to the PE moiety either as a fusion protein, or through a linker. Alternatively, the cell recognition domain can be located in place of, or within, domain III.

Most preferably, the cell recognition moiety is a polypeptide that binds to α2 macroglobulin receptor. Such polypeptides include, for example, natural ligands and antibodies. In a preferred embodiment, the cell recognition domain is the native sequence of domain Ia of PE, which binds α2 macroblogulin receptor. In another embodiment, the cell recognition moiety is α2 macroglobulin. In other embodiment the cell recognition moiety is an antibody that recognizes the α2 MR. Preferably, one chain of the immunoglobulin is produced as a fusion protein with the PE moiety. Included among such fusion proteins are single chain Fv fragments (scFv). In one embodiment, domain Ia is replaced with a polypeptide sequence for an immunoglobulin heavy chain from an immunoglobulin specific for the target receptor. The light chain of the immunoglobulin can be co-expressed with the PE conjugate so as to form a light chain-heavy chain dimer. In the conjugate protein, the antibody is chemically linked to a polypeptide comprising the other domains of the chimeric immunogen.

Attachment of cell specific ligands also can be accomplished through the use of linkers. The linker is capable of forming covalent bonds or high-affinity non-covalent bonds to both molecules. Suitable linkers are well known to those of ordinary skill in the art and include, but are not limited to, straight or branched-chain carbon linkers, heterocyclic carbon linkers, or peptide linkers. The linkers may be joined to the constituent amino acids through their side groups (e.g., through a disulfide linkage to cysteine).

Several methods are useful for identifying functional cell recognition moieties for use in chimeric immunogens. One method involves detecting binding between a conjugate that comprises the cell recognition moiety with the receptor or with a cell bearing the receptor. Other methods involve detecting transfer of the conjugate to the basal side of the membrane, indicating that the first step, cell binding, was successful. These methods are described in detail below in the section on testing.

C. PE Moiety

In certain embodiments, the bioconjugates of this invention further include a PE moiety. Such conjugates are referred to as "PE conjugates." PE conjugates also comprise an amino acid sequence encoding a "PE moiety." The PE moiety comprises amino acid sequences from PE domain II, PE domain III and, optionally, PE domain Ib. The amino acid sequences are sufficient to effect translocation of PE conjugates from the apical surface to the cytosol during their passage to the basal side of the membrane.

The PE moiety comprises sequences from PE domain II. This domain spans amino acids 253-364. The PE moiety can include the entire sequence of domain II. However, the entire sequence is not necessary for translocation. For example, the amino acid sequence can minimally contain, e.g., amino acids 280-344 of domain II of PE. Sequences outside this region, i.e., amino acids 253-279 and/or 345-364, can be eliminated from the domain. This domain also can be engineered with substitutions so long as translocation activity is retained.

The PE moiety can optionally comprise the PE Ib domain. In native *Pseudomonas* exotoxin A, domain Ib spans amino acids 365 to 399 of SEQ ID NO:2 and is located between PE domain II and PE domain III. The native Ib domain is structurally characterized by a disulfide bond between two cysteines at positions 372 and 379. Domain Ib is not essential for cell binding or translocation. Therefore, it can be re-engineered or eliminated completely. For example, the domain can be replaced with other amino acid sequences of up to about 1500 amino acids. The PE Ib domain can be linear or it can include a cysteine-cysteine loop. However, the conjugate preferably retains the native PE Ib domain because such constructs require less engineering to prepare.

In native PE, domain III has three functions. First, the amino-terminal portion of it, amino acids 400 to about 470, appear to be involved in translocation. Second, domain III exhibits ADP-ribosylating activity. Third, PE domain III includes the ER retention sequence, which directs endocytosed toxin into the endoplasmic reticulum.

The PE moiety generally will include those portions of PE domain III necessary for translocation and will preferably exclude other portions of the domain. For example, the PE moiety generally will include at least 70 amino acids from the amino-terminal portion of PE domain III (amino acids 400-470 from SEQ ID NO:2).

The ribosylating activity of PE is located between about amino acids 400 and 600 of PE. The bioactive conjugates of this invention preferably are non-toxic. In these embodiments, the ribosylating activity is abolished. Preferably, this is accomplished by eliminating PE domain III sequences beyond about amino acid 470 (SEQ ID NO:2). Alternatively, ADP ribosylation activity can be eliminated by deleting amino acid E553 ("ΔE553"). M. Lukac et al. (1988) *Infect. and Immun.* 56:3095-3098.

PE domain III includes at its carboxy-terminus, the endoplasmic reticulum retention sequence. The ER retention sequence has the sequence REDLK (amino acids 609-613 of SEQ ID NO:2). This sequence functions to retain PE within the cell. Because this function is not necessary in the PE conjugates of this invention, the ER sequence is preferably eliminated.

The PE moiety functions as follows. After binding to a receptor on the cell surface, the chimeric proteins enter the cell by endocytosis through clathrin-coated pits. Residues 265 and 287 are cysteines that form a disulfide loop. Once internalized into endosomes having an acidic environment, the peptide is cleaved by the protease furin between Arg279 and Gly280. Then, the disulfide bond is reduced. A mutation at Arg279 inhibits proteolytic cleavage and subsequent translocation to the cytosol. M. Ogata et al. (1990) *J. Biol. Chem.* 265:20678-85. However, a fragment of PE containing the sequence downstream of Arg279 (called "PE37") retains substantial ability to translocate to the cytosol. C. B. Siegall et al. (1989) *J. Biol. Chem.* 264:14256-61. Sequences in PE domain II beyond amino acid 345 also can be deleted without inhibiting translocation. Furthermore, amino acids at positions 339 and 343 appear to be necessary for translocation. C. B. Siegall et al. (1991) *Biochemistry* 30:7154-59.

In preferred embodiments the amino acid sequence of the PE moiety is a contiguous sequence from PE. In this embodiment, the PE moiety minimally comprises amino acids 253 to 470 of PE (SEQ ID NO:2). In other preferred embodiments, the cell recognition moiety and the PE moiety, together, are taken from PE. Thus, these two moieties can comprise the sequence of amino acids 1-470 of PE (SEQ ID NO:2).

Methods for determining the functionality of the PE moiety are described below in the section on testing.

D. Bioactive Moiety

The conjugates of this invention include a "bioactive moiety" comprising a bioorganic molecule, such as a polypeptide, nucleic acid, carbohydrate or lipid. The bioactive moiety (a) has a biological activity selected from receptor binding, cytokine activity, enzymatic activity, hormonal activity, interleukin activity, neurotransmitter activity, regulation of transcription or translation and affinity for another bioorganic ic molecule (e.g., an immunoglobulin), (b) does not function solely as an immunogen to invoke an immune response and (c) does not have ADP ribosylating activity. The purpose of the conjugates of this invention is to deliver the bioactive moiety to the sub-mucosal space, where it can exercise its proper pharmacological activity.

In preferred embodiments, the bioactive moiety comprises a polypeptide. The polypeptide portion of the bioactive moiety can comprise any polypeptide or protein of interest. The polypeptide may, itself, possess the desired biological activity, such as cytokines, interleukins, enzymes, ligands for cell receptors, inhibitors of angiogenesis, antibodies that bind to and block the activity of target receptors or antigens. Alternatively, the polypeptide can function as a carrier of another molecule of interest which exhibits the bioactivity. For example, the polypeptide can be a DNA binding protein, a carbohydrate binding protein (a lectin), a lipid binding protein or a protein ligand or receptor. Accordingly, the active moiety can be used to deliver a nucleic acid, a carbohydrate, a lipid or another protein of interest.

Most preferred polypeptides for the bioactive moiety are those pharmaceutical proteins that presently are introduced parenterally by injection. These include, for example, insulin, interferons (e.g., α-interferon, β-interferon, γ-interferon), growth hormone, erythropoietin, tissue plasminogen activator, granulocyte colony stimulating factor (G-CSF), granulocyte macrophage colony stimulating factor (GM-CSF), interleukins (e.g., Il-1, Il-2 or tumor necrosis factor (TNF)), clotting factor VIII or glucocerebrosidase.

The bioactive moiety can be chemically coupled to the conjugate. However, it is preferable to engineer the conjugate as a single fusion protein containing the cell recognition moiety, the PE moiety and the active moiety. Means for attaching the polypeptide moiety to the conjugate, either chemically or genetically, are described below.

The bioactive moiety can be attached to the conjugate at any location as long as it does not interfere with translocation or cell binding activity. In one embodiment, the bioactive moiety is coupled directly to a cell recognition molecule, such as domain 1a of PE or an antibody against α2-MR. In a PE conjugate of this invention, the relative position of the three moieties is, from the amino terminus: cell recognition moiety—PE moiety—bioactive moiety. In such an embodiment, much of PE domain III can be eliminated from PE and replaced with the polypeptide portion of the active moiety.

However, other arrangements are possible. For example, the active moiety can be positioned at the amino-terminus and the cell recognition domain can be attached at the carboxy-terminus. However, the active moiety should not interfere with the function of the cell recognition moiety. Therefore, when the cell recognition moiety is derived from, or is positioned at the location of PE domain Ia, the active moiety preferably is placed in the location of PE domain III. Alternatively, but less preferably, when the cell recognition domain is located in place of PE domain III, the active moiety can be positioned in place of PE domain Ia.

In choosing the location of the active moiety, the nature of the polypeptide should be taken into account. For example, in proteins in which a free amino-terminal end is necessary for activity (for example, growth hormone), the polypeptide is best fused to the conjugate at the carboxy-terminal end. In such an embodiment, the polypeptide should replace PE domain Ia, and the cell recognition domain should replace portions of PE domain III.

In one embodiment, the active moiety is connected to the cell recognition moiety or the PE moiety by means of a polypeptide linker that comprises a protease-cleavable site. In this way, the active moiety can be released from the conjugate by the action of a protease. Preferably, this site is recognized by a protease present in the cell or at the basal surface of the epithelium. In that case, the moiety is released upon traversing the membrane. For example, the protease activatable sequence can be Pro-Leu-Gly-Met-Trp-Ser-Arg (SEQ ID NO:3) which is recognized by gelatinase. Also, it could be Arg-Pro-Leu-Ala-Leu-Trp-Arg-Ser (SEQ ID NO:4) which is recognized by collagenase.

Activity of this domain can be assessed by testing for translocation of the protein into the target cell cytosol using the assays described below.

In another embodiment, a cell recognition moiety is inserted into the amino acid sequence of the ER retention domain (e.g., into domain III). For example, the cell recognition moiety can be inserted just up-stream of the ER retention sequence, so that the ER retention sequence is connected directly or within ten amino acids of the carboxy terminus of the cell recognition moiety.

III. Making Bioactive Conjugates

Bioconjugates preferably are produced recombinantly as fusion proteins. Bioactive conjugates also can be made by chemical synthesis.

A. Recombinant Polynucleotides Encoding Bioactive Conjugates

1. Recombinant Polynucleotides a. Sources

This invention provides recombinant polynucleotides comprising a nucleotide sequence encoding the conjugates of this invention. These polynucleotides are useful for making the conjugates. The recombinant polynucleotides of this invention which encode bioactive conjugates are based on polynucleotides encoding *Pseudomonas* exotoxin A, or portions of it. A nucleotide sequence encoding PE is presented above. The practitioner can use this sequence to prepare PCR primers for isolating a full-length sequence. The sequence of PE can be modified to engineer a polynucleotide encoding the PE conjugate.

A polynucleotide encoding PE or any other polynucleotide used in the chimeric proteins of the invention can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of PE or a cell recognition molecule.

A wide variety of cloning and in vitro amplification methodologies are well-known to persons skilled in the art. PCR methods are described in, for example, U.S. Pat. No. 4,683,195; Mullis et al. (1987) *Cold Spring Harbor Symp. Quant. Biol.* 51:263; and Erlich, ed., PCR TECHNOLOGY, (Stockton Press, NY, 1989). Polynucleotides also can be isolated by screening genomic or cDNA libraries with probes selected from the sequences of the desired polynucleotide under stringent hybridization conditions.

b. Engineered Versions

Engineered versions of the conjugates can be made by site-specific mutagenesis of other polynucleotides encoding the proteins, or by random mutagenesis caused by increasing the error rate of PCR of the original polynucleotide with 0.1 mM $MnCl_2$ and unbalanced nucleotide concentrations.

Eliminating nucleotides encoding amino acids 1-252 yields a construct referred to as "PE40." Eliminating nucleotides encoding amino acids 1-279 yields a construct referred to as "PE37." (See, U.S. Pat. No. 5,602,095 (Pastan et al.).) The practitioner can ligate sequences encoding cell recognition moieties to the 5' end of these platforms to engineer PE-like chimeric proteins that are directed to particular cell surface receptors. These constructs optionally can encode an amino-terminal methionine. A cell recognition moiety can be inserted into such constructs in the nucleotide sequence encoding the ER retention domain.

2. Expression Vectors

This invention also provides expression vectors for expressing bioactive conjugates. Expression vectors are recombinant polynucleotide molecules comprising expression control sequences operatively linked to a nucleotide sequence encoding a polypeptide. Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., MOLECULAR CLONING—A LABORATORY MANUAL, Cold Spring Harbor Laboratory, Cold Spring Harbor, N.Y., (1989) and CURRENT PROTOCOLS IN MOLECULAR BIOLOGY, F. M. Ausubel et al., eds., (Current Protocols, a joint venture between Greene Publishing Associates, Inc. and John Wiley & Sons, Inc.) Useful promoters for such purposes include a metallothionein promoter, a constitutive adenovirus major late promoter, a dexamethasone-inducible MMTV promoter, a SV40 promoter, a MRP polIII1 promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes.

Expression vectors useful in this invention depend on their intended use. Such expression vectors must, of course, contain expression and replication signals compatible with the host cell. Expression vectors useful for expressing bioactive conjugates include viral vectors such as retroviruses, adenoviruses and adeno-associated viruses, plasmid vectors, cosmids, and the like. Viral and plasmid vectors are preferred for transfecting mammalian cells. The expression vector pcDNA1 (Invitrogen, San Diego, Calif.), in which the expression control sequence comprises the CMV promoter, provides good rates of transfection and expression. Adeno-associated viral vectors are useful in the gene therapy methods of this invention.

A variety of means are available for delivering polynucleotides to cells including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. See also U.S. Pat. No. 5,272,065 (Inouye et al.); METHODS IN ENZYMOLOGY, vol. 185, Academic Press, Inc., San Diego, Calif. (D. V. Goeddel, ed.) (1990) or M. Krieger, GENE TRANSFER AND EXPRESSION—A LABORATORY MANUAL, Stockton Press, New York, N.Y., (1990). Recombinant DNA expression plasmids can also be used to prepare the polynucleotides of the invention for delivery by means other than by gene therapy, although it may be more economical to make short oligonucleotides by in vitro chemical synthesis.

The construct can also contain a tag to simplify isolation of the protein. For example, a polyhistidine tag of, e.g., six histidine residues, can be incorporated at the amino terminal end of the protein. The polyhistidine tag allows convenient isolation of the protein in a single step by nickel-chelate chromatography.

3. Recombinant Cells

The invention also provides recombinant cells comprising an expression vector for expression of the nucleotide sequences encoding a PE chimeric immunogen of this invention. Host cells can be selected for high levels of expression in order to purify the protein. The cells can be prokaryotic cells, such as *E. coli*, or eukaryotic cells. Useful eukaryotic cells include yeast and mammalian cells. The cell can be, e.g., a recombinant cell in culture or a cell in vivo.

*E. coli* has been successfully used to produce PE conjugates. The protein can fold and disulfide bonds can form in this cell.

B. Chemical Synthesis

Long polypeptides, such as the fusion proteins of this invention, can be chemically synthesized by emerging processes. One such process is described in W. Lu et al., *Federation of European Biochemical Societies Letters.* 429:31-35 (1998).

Also, the conjugates of this invention can be prepared not as fusion proteins, but as chemical conjugates in which various functional moieties are chemically coupled. Methods for chemical coupling are well known in the art.

The procedure for chemically coupling moieties of a *Pseudomonas* exotoxin conjugate will vary according to the chemical structure of the conjugate. Antibodies contain a variety of functional groups; e.g., sulfhydryl (—S), carboxylic acid (COOH) or free amine (—$NH_2$) groups, which are available for reaction with a suitable functional group on a conjugate. Additionally, or alternatively, the antibody or *Pseudomonas* exotoxin conjugate can be derivatized to expose or attach additional reactive functional groups. The derivitization may involve attachment of any of a number of linker molecules such as those available from Pierce Chemical Company, Rockford Ill.

A bifunctional linker having one functional group reactive with a group on the *Pseudomonas* exotoxin conjugate, and another group reactive with a cell specific ligand, can be used to form a desired conjugate. Alternatively, derivitization may involve chemical treatment of the *Pseudomonas* exotoxin conjugate or the cell specific ligand, e.g., glycol cleavage of the sugar moiety of a glycoprotein antibody with periodate to generate free aldehyde groups. The free aldehyde groups on the antibody may be reacted with free amine or hydrazine groups on the antibody to bind the *Pseudomonas* exotoxin conjugate thereto. (See U.S. Pat. No. 4,671,958 (J. D. Rodwell et al.)) Procedures for generation of free sulfhydryl groups on antibodies or other proteins, are also known. (See U.S. Pat. No. 4,659,839 (R. A. Nicoletti et al.).)

In one embodiment, the PE moiety is derivatized by adding an amino acid residue with a reactive group, such as lysine, arginine or cysteine, near the carboxy or amino terminus of the molecule. When the residue contains an active amine group, the cell recognition moiety or the active moiety can be coupled through a bi-functional linker that reacts with the amine group on the lysine. In the case of cysteine, the sulfur atom can be used as the basis of a disulfide bond between the PE moiety and the cell recognition moiety or the active moiety.

IV. Testing Bioactive Conjugates

Having selected various structures as moieties of the PE conjugate, the function of these moieties, and of the conjugate as a whole, can be tested to detect functionality. Bioactive conjugates can be tested for cell recognition, translocation across the epithelial cell layer and biological activity of the active moiety using routine assays. The entire chimeric protein can be tested, or, the function of various domains can be tested by substituting them for native domains of the wild-type toxin.

A. Receptor Binding/Cell Recognition

The function of the cell binding domain can be tested as a function of the conjugate to bind to the target receptor either isolated or on the cell surface.

In one method, binding of the conjugate to a target is performed by affinity chromatography. For example, the conjugate can be attached to a matrix in an affinity column, and binding of the receptor to the matrix detected.

Binding of the conjugate to receptors on cells can be tested by, for example, labeling the conjugate and detecting its binding to cells by, e.g., fluorescent cell sorting, autoradiography, etc.

If antibodies have been identified that bind to the ligand from which the cell recognition moiety is derived, they also are useful to detect the existence of the cell recognition moiety in the chimeric immunogen by immunoassay, or by competition assay for the cognate receptor.

B. Translocation to the Basal Surface

The function of the PE moiety can be tested by determining the ability of the conjugate to translocate across an epithelial cell layer. Because access first requires binding to the cell, these assays also are useful to determine whether the cell recognition moiety is functioning. Translocation can be tested in vitro or in vivo.

In one method, access to the cytosol is determined by detecting the physical presence of the conjugate in the cytosol. For example, the conjugate can be labeled and the conjugate exposed to the cell. Then, the cytosolic fraction is isolated and the amount of label in the fraction determined. Detecting label in the fraction indicates that the conjugate has gained access to the cytosol.

In another method, the ability to translocate across the membrane is performed using a membrane cultured in vitro. Van Deurs et al. *Europ. J. Cell Biol.* 1990 51:96 described a model system for polar epithelial cells. In the model system, MDCK cells are seeded on a permeable filter. The conjugates of this invention can be tested by the model. The proteins are placed into contact with the apical surface of the membrane. Then, the opposite side of the permeable filter is checked for transmission of the conjugate.

In another method, the conjugate can be administered to a mucosal surface of a test animal and its presence in the system or on the basal surface can be detected.

C. Activity of the Bioactive Moiety

The function of active moiety also can be tested.

In vitro, the bioactive moiety attached to the conjugate can be tested for activity by any established assay useful to test the activity of the moiety. For example, if the moiety is an enzyme, the activity of the enzyme can be tested in an enzymatic assay. Or, if the bioactive moiety is a cytokine, its activity can be tested in any established test of the ability of the cytokine to alter cell activity.

When the conjugate includes a protease cleavable site, one can test the ability of the target enzyme to cleave the active moiety from the conjugate. Then the activity of the moiety can be tested as above.

The activity of the moiety can be tested after passage across an epithelial cell layer to determine it the conjugate has retained activity. In an in vitro method, the polar epithelial cell layer model, described above, is used. Conjugate is allowed to pass through the epithelial cell layer, collected, and tested for the activity of the active moiety.

In another method, the activity is tested in vivo. In this method, the conjugate is applied to an epithelial surface of an animal model, such as a mouse. Then, the activity of the conjugate in the animal is tested.

V. Use of Bioactive Conjugates

The bioactive conjugates of this invention delivering active biologically active molecules systemically without injection. Therefore, they are useful for any prophylactic or therapeutic treatment, or diagnostic method that requires the introduction of proteins into the body. Furthermore, while the conjugates of this invention, upon introduction, enter the circulation, because they access the body at the sub-mucosal space, they are especially useful for targeting cells located in the submucosal space and cells that traffic through it. This includes, for example, cells of the immune system which traffic to the lymph nodes (e.g., lymphocytes, macrophages, other leukocytes), nerve cells and muscle cells.

The conjugates of this invention obviate the need for injection of proteins therefore, they are particularly useful for the treatment of chronic diseases treated with protein pharmaceuticals. The conjugates of this invention are preferred for the treatment of chronic conditions rather than acute ones because the protein cannot be delivered through the mucosa as quickly as through injection. For example, in the treatment of diabetes, the conjugate can include insulin as an active moiety. In the treatment of multiple sclerosis, the active moiety can be β-interferon. For the treatment of red blood cell deficiency, for example, that resulting from radiation therapy, the active moiety can be erythropoietin. For the prophylactic treatment of infections (by the stimulation of leukocyte production) in chemotherapy, the active moiety can be granulocyte colony stimulating factor (G-CSF). For the treatment of hepatitis or herpes infections, the active moiety can be α-interferon. For the treatment of hemophilia, the active moiety can be a clotting factor, such as factor VIII. For the treatment of growth disorders or for increasing lean muscle mass, the active moiety can be human growth hormone. For promoting hematopoiesis, the active moiety can comprise granulocyte macrophage colony stimulating factor (GM-CSF).

In a therapeutic method of the invention, the bioactive moiety comprises a targeting moiety that binds to a target cell of interest, for example, an antigen on a cancer cell. The bioactive moiety also will include a toxic component that will inhibit the growth of, or kill the target cell.

In another embodiment, the bioactive conjugates of this invention are useful as diagnostics. In this case, the bioactive moiety comprises a diagnostic component. For example, the diagnostic component can include a ligand that binds to a target cell, for example a cancer cell, and a detectable moiety. In general, any conventional method for visualizing diagnostic imaging can be used. For example, binding can be detected by, for example, magnetic resonance imaging (MRI) or electron spin resonance (ESR). Usually gamma-emitting and positron-emitting radioisotopes are used for camera imaging and paramagnetic isotopes are used for magnetic resonance imaging.

VI. Pharmaceutical Compositions and Modes of Delivery

The bioactive conjugates of this invention preferably are delivered as pharmaceutical compositions to mucosal surfaces of the subject. The compounds of the invention are formulated for administration to a mucosal surface in a variety of ways. Typical routes of administration include oral, sublingual, nasal, vaginal or anal. The mode of administration can be, e.g., via swallowing, inhalation or topical application to a mucosal surface. Particular formulations typically are appropriate for specific modes of administration. Various contemplated formulations include, for example, aqueous solutions, solid formulations and aerosol formulations.

A. Aqueous Solutions for Enteral, Parenteral or Transmucosal Administration

Examples of aqueous solutions include, for example, water, saline, phosphate buffered saline, Hank's solution, Ringer's solution, dextrose/saline, glucose solutions and the like. The compositions can contain pharmaceutically acceptable auxiliary substances as required to approximate physiological conditions or to improve stability, appearance or ease of administration, such as buffering agents, tonicity adjusting agents, wetting agents, detergents and the like. Additives can also include additional active ingredients such as bactericidal agents, or stabilizers. For example, the solution can contain sodium acetate, sodium lactate, sodium chloride, potassium chloride, calcium chloride, sorbitan monolaurate or triethanolamine oleate. These compositions can be sterilized by conventional, well-known sterilization techniques, or can be sterile filtered. The resulting aqueous solutions can be packaged for use as is, or lyophilized, the lyophilized preparation being combined with a sterile aqueous solution prior to administration.

B. Topical Administration for Transmucosal Delivery

Systemic administration can also be by transmucosal means. For transmucosal administration, penetrants appropriate to the barrier to be permeated are used in the formulation. Such penetrants are generally known in the art, and include, for example, bile salts and fusidic acid derivatives. In addition, detergents can be used to facilitate permeation. Transmucosal administration can be through nasal sprays, for example, or using suppositories in the anus or vagina.

The carrier can be selected from various oils including those of petroleum, animal, vegetable or synthetic origin, for example, peanut oil, soybean oil, mineral oil, sesame oil, and the like. Suitable pharmaceutical excipients include any materials generally regarded as safe, such as starch, cellulose, talc, glucose, lactose, sucrose, gelatin, maltose, rice, flour, chalk, silica gel, magnesium stearate, sodium stearate, glycerol monostearate, sodium chloride, dried skim milk, glycerol, propylene glycol, water, ethanol, and the like.

For topical administration, the agents are formulated into ointments, creams, salves, powders and gels. In one embodiment, the transdermal delivery agent can be DMSO.

C. Delivery by Inhalation

For inhalation, the compound is preferably administered in the form of an aerosol, liquid or solid. For aerosol administration, the compound preferably is supplied in finely divided form along with a surfactant and propellant. A surfactant may be required if the agent is immiscible in the propellant.

The surfactant preferably is soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides, can be employed. The surfactant can constitute 0.1%-20% by weight of the composition, preferably 0.25%-5%.

The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the agent as a solution or as finely divided particles and surfactant. The ingredients are thus maintained at an elevated pressure until released by action of the valve.

A nebulizer or aerosolizer device for administering compounds typically delivers a dose of about concentration of between about 1 and 50 mg per inhalation.

D. Other Formulations

In preparing pharmaceutical compositions of the present invention, it can be desirable to modify the complexes of the present invention to alter their pharmacokinetics and biodistribution. For a general discussion of pharmacokinetics, See, REMINGTON'S PHARMACEUTICAL SCIENCES, supra, Chapters 37-39. A number of methods for altering pharmacokinetics and biodistribution are known to one of ordinary skill in the art. Examples of such methods include protection of the complexes in vesicles composed of substances such as proteins, lipids (for example, liposomes), carbohydrates, or synthetic polymers.

VII. Administration

Single or multiple administrations of the compositions can be carried out with dose levels and pattern being selected by the treating physician. In any event, the pharmaceutical formulations should provide a quantity of a compound sufficient to treat the patient effectively.

The conjugates of this invention can be administered to any accessible mucosal surface. This includes, for example, epithelial surfaces of the respiratory system (e.g., nose or lungs), gastrointestinal system (e.g., mouth, intestine, rectal or anus), reproductive system (e.g., vagina or urethra) or any other epithelial surface such as sebaceous glands, ears and eyes.

The total effective amount of a compound of the present invention can be administered to a subject as a single dose or can be administered using a fractionated treatment protocol, in which the multiple doses are administered over a more prolonged period of time. One skilled in the art would know that the concentration of a compound of the present invention required to obtain an effective dose in a subject depends on many factors including the age and general health of the subject, the route of administration, the number of treatments to be administered and the judgment of the prescribing physician. In view of these factors, the skilled artisan would adjust the dose so as to provide an effective dose for a particular use.

In general, the amount of conjugate delivered will be between about 10 mg and 100 mg. In aqueous solutions the amount of the conjugate can be about 1 mg/ml to about 100 mg/ml, more preferably about 10 mg/ml. The bioactive conjugates of this invention gain access by binding to epithelial receptors. Therefore, the amount of conjugate applied to the mucosal surface optimally is enough to saturate the receptors. Amounts beyond this will not gain access any faster.

The present invention provides novel bioactive conjugates and methods for using them for parenteral administration of proteins without injection. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document Applicants do not admit that any particular reference is "prior art" to their invention.

What is claimed is:

1. A method of systemically delivering an effective dose of a bioactive moiety to produce a systemic effect in a mammal in need thereof, said method comprising contacting a mucosal membrane of the mammal with a recombinant protein drug that comprises:

(1) a cell recognition moiety that binds to an α2 macroglobulin receptor, and (2) the bioactive moiety, which:

(a) has a biological activity that mediates the systemic effect of the bioactive moiety and is selected from receptor binding, cytokine activity, enzymatic activity, interleukin activity, neurotransmitter activity, regulation of transcription and affinity for a bioorganic molecule, (b) does not function as an immunogen in producing the needed systemic effect, and (c) does not have ADP ribosylating activity, wherein, the bioactive moiety is translocated across the mucosal membrane of a mammal from the apical surface of the membrane through the basal surface of the membrane to enter a sub-membrane space below the mucosal membrane in an amount which delivers an effective dose of the protein drug to the mammal to produce the systemic effect; and further, wherein, when the protein drug comprises a *Pseudomonas* exotoxin moiety, the *Pseudomonas* exotoxin moiety is noncytotoxic.

2. The method of claim 1, wherein the mammal is a human.

3. The method of claim 1, wherein the mucosal membrane is a mucosal membrane selected from the group consisting of mucosal membranes of the gastrointestinal system, the respiratory system and the reproductive system.

4. The method of claim 1, wherein the bioactive moiety of the protein drug comprises a polypeptide selected from the group consisting of an interferon, a growth hormone, an erythropoietin and insulin.

5. The method of claim 1, wherein the bioactive moiety of the protein drug comprises a polypeptide that is an enzyme.

6. The method of claim 1, wherein the bioactive moiety of the protein drug comprises a polypeptide selected from the group consisting of an antibody, a lectin, a DNA binding protein, a lipid binding protein and a ligand for a cell surface receptor.

7. The method of claim 1, wherein the protein drug further comprises a cleavage site recognized by a protease, and wherein cleavage by the protease releases the bioactive moiety from the protein drug.

8. The method of claim 7, wherein the cleavage site recognized by the protease comprises an amino acid sequence connecting the cell recognition domain with the bioactive moiety.

9. The method of claim 1, wherein the protease is a protease located at the basal surface of the mucosal membrane.

10. The method of claim 1, wherein the cell recognition moiety of the protein drug comprises an antibody that binds the α2-macroglobulin receptor.

11. The method of claim 1, wherein the cell recognition moiety of the protein drug comprises the amino acid sequence of SEQ ID NO:2 from position 1 to 252.

12. The method of claim 11, wherein the protein drug further comprise the amino sequence of SEQ ID NO:2 from position 253-364 or from position 280 to 364 and the amino acid sequence of SEQ ID NO:2 from position 400 to 470, and optionally, the amino acid sequence of SEQ ID NO:2 from position 365 to 399.

13. The method of claim 12, wherein the protein drug comprises the amino acid sequence of SEQ ID NO:2 from position 365 to 399.

14. The method of claim 1, wherein the protein drug comprises:
(a) the amino acid sequence of SEQ ID NO:2 from position 280 to 344;
(b) the amino acid sequence of SEQ ID NO:2 from position 400 to about 470; and optionally,
(c) domain Ib of *Pseudomonas* exotoxin A.

15. The method of claim 1, wherein the protein drug comprises the amino acid sequence of SEQ ID NO:2 from position 280 to 344.

16. The method of claim 1, wherein the protein drug comprises the amino acid sequence of SEQ ID NO:2 from position 400 to about 470.

17. The method of claim 1, wherein the protein drug is a non-toxic bioactive conjugate.

18. A recombinant protein drug comprising:
(1) a cell recognition moiety that is capable of binding to the α2 macroglobulin receptor, and
(2) a bioactive moiety that is capable of providing a therapeutic systemic effect and which
(a) has a biological activity that mediates the systemic effect and is selected from receptor binding, cytokine activity, enzymatic activity, interleukin activity, neurotransmitter activity, regulation of transcription and affinity for a bioorganic molecule, and the bioactive moiety does not function as an immunogen in producing the systemic effect,
wherein the protein drug does not have ADP ribosylating activity and is capable of translocating across the mucosal membrane of a mammal from the apical surface of the membrane through the basal surface of the membrane to enter a sub-membrane space below the mucosal membrane and further, wherein, when the protein drug comprises a *Pseudomonas* exotoxin moiety, the *Pseudomonas* exotoxin moiety is noncytotoxic;
wherein the protein drug further comprises a cleavage site recognized by a protease at the basal surface of mucosal epithelium, and wherein the cleavage site is located to release the bioactive moiety from the protein drug upon cleavage by the protease.

19. The protein drug of claim 18, wherein the protein drug comprises the amino sequence of SEQ ID NO:2 from position 253-364 or from position 280 to 364 and the amino acid sequence of SEQ ID NO:2 from position 400 to 470, and optionally, the amino acid sequence of SEQ ID NO:2 from position 365 to 399.

20. The protein drug of claim 18, wherein the protein drug is a non-toxic bioactive conjugate.

21. A pharmaceutical composition comprising a recombinant protein drug that comprises:
(1) a cell recognition moiety that is capable of binding to the α2 macroglobulin receptor, and
(2) a bioactive moiety that is capable of providing a therapeutic systemic effect and which
(a) has a biological activity that mediates the systemic effect and is selected from receptor binding, cytokine activity, enzymatic activity, interleukin activity, neurotransmitter activity, regulation of transcription and affinity for a bioorganic molecule,
(b) does not function as an immunogen in producing the systemic effect, and
(c) does not have ADP ribosylating activity,
wherein the protein drug further comprises a cleavage site recognized by a protease, which cleavage site is located to release the bioactive moiety from the protein drug upon cleavage by the protease; and further, wherein, when the protein drug comprises a *Pseudomonas* exotoxin moiety, the *Pseudomonas* exotoxin moiety is non-cytotoxic;
wherein the composition is formulated for contacting with the mucosa of a mammal, and
wherein the composition contains a pharmacologically effective amount of the protein drug with respect to the systemic effect.

22. The pharmaceutical composition of claim 21, wherein the protease is a protease at the basal surface of mucosal epithelium.

23. The pharmaceutical composition of claim 21, wherein the protein drug comprises the amino sequence of SEQ ID NO:2 from position 253-364 or from position 280 to 364 and the amino acid sequence of SEQ ID NO:2 from position 400 to 470, and optionally, the amino acid sequence of SEQ ID NO:2 from position 365 to 399.

24. The pharmaceutical composition of claim 21, wherein the protein drug comprises the amino acid sequence of SEQ ID NO:2 from position 280 to 344.

25. The pharmaceutical composition of claim 21, wherein the protein drug comprises the amino acid sequence of SEQ ID NO:2 from position 400 to about 470.

26. The composition of claim 21, wherein the protein drug is a non-toxic bioactive conjugate.

27. A recombinant nucleic acid encoding the prodrug of claim 18.

28. A recombinant nucleic acid encoding the prodrug of claim 19.

29. The nucleic acid of claim 27, wherein the protein drug comprises the amino acid sequence of SEQ ID NO:2 from position 280 to 344.

30. The nucleic acid of claim 27, wherein the protein drug comprises the amino acid sequence of SEQ ID NO:2 from position 400 to about 470.

* * * * *

SEQUENCE LISTING

```
<160> NUMBER OF SEQ ID NOS: 5

<210> SEQ ID NO 1
<211> LENGTH: 1839
<212> TYPE: DNA
<213> ORGANISM: Pseudomonas aeruginosa
<220> FEATURE:
<221> NAME/KEY: CDS
<222> LOCATION: (1)..(1839)
<223> OTHER INFORMATION: exotoxin A

<400> SEQUENCE: 1 gcc gaa gaa gct ttc gac ctc tgg aac gaa tgc gcc aaa gcc tgc gtg        48
Ala Glu Glu Ala Phe Asp Leu Trp Asn Glu Cys Ala Lys Ala Cys Val
  1               5                  10                  15 ctc gac ctc aag gac ggc gtg cgt tcc agc cgc atg agc gtc gac ccg        96
Leu Asp Leu Lys Asp Gly Val Arg Ser Ser Arg Met Ser Val Asp Pro
             20                  25                  30 gcc atc gcc gac acc aac ggc cag ggc gtg ctg cac tac tcc atg gtc       144
Ala Ile Ala Asp Thr Asn Gly Gln Gly Val Leu His Tyr Ser Met Val
         35                  40                  45 ctg gag ggc ggc aac gac gcg ctc aag ctg gcc atc gac aac gcc ctc       192
Leu Glu Gly Gly Asn Asp Ala Leu Lys Leu Ala Ile Asp Asn Ala Leu
     50                  55                  60 agc atc acc agc gac ggc ctg acc atc cgc ctc gaa ggc ggc gtc gag       240
Ser Ile Thr Ser Asp Gly Leu Thr Ile Arg Leu Glu Gly Gly Val Glu
 65                  70                  75                  80 ccg aac aag ccg gtg cgc tac agc tac acg cgc cag gcg cgc ggc agt       288
Pro Asn Lys Pro Val Arg Tyr Ser Tyr Thr Arg Gln Ala Arg Gly Ser
                 85                  90                  95 tgg tcg ctg aac tgg ctg gta ccg atc ggc cac gag aag ccc tcg aac       336
Trp Ser Leu Asn Trp Leu Val Pro Ile Gly His Glu Lys Pro Ser Asn
            100                 105                 110 atc aag gtg ttc atc cac gaa ctg aac gcc ggc aac cag ctc agc cac       384
Ile Lys Val Phe Ile His Glu Leu Asn Ala Gly Asn Gln Leu Ser His
        115                 120                 125 atg tcg ccg atc tac acc atc gag atg ggc gac gag ttg ctg gcg aag       432
Met Ser Pro Ile Tyr Thr Ile Glu Met Gly Asp Glu Leu Leu Ala Lys
    130                 135                 140 ctg gcg cgc gat gcc acc ttc ttc gtc agg gcg cac gag agc aac gag       480
Leu Ala Arg Asp Ala Thr Phe Phe Val Arg Ala His Glu Ser Asn Glu
145                 150                 155                 160 atg cag ccg acg ctc gcc atc agc cat gcc ggg gtc agc gtg gtc atg       528
Met Gln Pro Thr Leu Ala Ile Ser His Ala Gly Val Ser Val Val Met
                165                 170                 175
```

```
gcc cag acc cag ccg cgc cgg gaa aag cgc tgg agc gaa tgg gcc agc      576
Ala Gln Thr Gln Pro Arg Arg Glu Lys Arg Trp Ser Glu Trp Ala Ser
            180                 185                 190 ggc aag gtg ttg tgc ctg ctc gac ccg ctg gac ggg gtc tac aac tac      624
Gly Lys Val Leu Cys Leu Leu Asp Pro Leu Asp Gly Val Tyr Asn Tyr
                195                 200                 205 ctc gcc cag caa cgc tgc aac ctc gac gat acc tgg gaa ggc aag atc      672
Leu Ala Gln Gln Arg Cys Asn Leu Asp Asp Thr Trp Glu Gly Lys Ile
            210                 215                 220 tac cgg gtg ctc gcc ggc aac ccg gcg aag cat gac ctg gac atc aaa      720
Tyr Arg Val Leu Ala Gly Asn Pro Ala Lys His Asp Leu Asp Ile Lys
225                 230                 235                 240 ccc acg gtc atc agt cat cgc ctg cac ttt ccc gag ggc ggc agc ctg      768
Pro Thr Val Ile Ser His Arg Leu His Phe Pro Glu Gly Gly Ser Leu
                245                 250                 255 gcc gcg ctg acc gcg cac cag gct tgc cac ctg ccg ctg gag act ttc      816
Ala Ala Leu Thr Ala His Gln Ala Cys His Leu Pro Leu Glu Thr Phe
            260                 265                 270 acc cgt cat cgc cag ccg cgc ggc tgg gaa caa ctg gag cag tgc ggc      864
Thr Arg His Arg Gln Pro Arg Gly Trp Glu Gln Leu Glu Gln Cys Gly
        275                 280                 285 tat ccg gtg cag cgg ctg gtc gcc ctc tac ctg gcg gcg cgg ctg tcg      912
Tyr Pro Val Gln Arg Leu Val Ala Leu Tyr Leu Ala Ala Arg Leu Ser
            290                 295                 300 tgg aac cag gtc gac cag gtg atc cgc aac gcc ctg gcc agc ccc ggc      960
Trp Asn Gln Val Asp Gln Val Ile Arg Asn Ala Leu Ala Ser Pro Gly
305                 310                 315                 320 agc ggc ggc gac ctg ggc gaa gcg atc cgc gag cag ccg gag cag gcc     1008
Ser Gly Gly Asp Leu Gly Glu Ala Ile Arg Glu Gln Pro Glu Gln Ala
                325                 330                 335 cgt ctg gcc ctg acc ctg gcc gcc gcc gag agc gag cgc ttc gtc cgg     1056
Arg Leu Ala Leu Thr Leu Ala Ala Ala Glu Ser Glu Arg Phe Val Arg
            340                 345                 350 cag ggc acc ggc aac gac gag gcc ggc gcg gcc aac gcc gac gtg gtg     1104
Gln Gly Thr Gly Asn Asp Glu Ala Gly Ala Ala Asn Ala Asp Val Val
        355                 360                 365 agc ctg acc tgc ccg gtc gcc gcc ggt gaa tgc gcg ggc ccg gcg gac     1152
Ser Leu Thr Cys Pro Val Ala Ala Gly Glu Cys Ala Gly Pro Ala Asp
370                 375                 380 agc ggc gac gcc ctg ctg gag cgc aac tat ccc act ggc gcg gag ttc     1200
Ser Gly Asp Ala Leu Leu Glu Arg Asn Tyr Pro Thr Gly Ala Glu Phe
385                 390                 395                 400 ctc ggc gac ggc ggc gac gtc agc ttc agc acc cgc ggc acg cag aac     1248
Leu Gly Asp Gly Gly Asp Val Ser Phe Ser Thr Arg Gly Thr Gln Asn
                405                 410                 415 tgg acg gtg gag cgg ctg ctc cag gcg cac cgc caa ctg gag gag cgc     1296
Trp Thr Val Glu Arg Leu Leu Gln Ala His Arg Gln Leu Glu Glu Arg
            420                 425                 430 ggc tat gtg ttc gtc ggc tac cac ggc acc ttc ctc gaa gcg gcg caa     1344
Gly Tyr Val Phe Val Gly Tyr His Gly Thr Phe Leu Glu Ala Ala Gln
        435                 440                 445 agc atc gtc ttc ggc ggg gtg cgc gcg cgc agc cag gac ctc gac gcg     1392
Ser Ile Val Phe Gly Gly Val Arg Ala Arg Ser Gln Asp Leu Asp Ala
450                 455                 460 atc tgg cgc ggt tta tat atc gcc ggc gat ccg gcg ctg gcc tac ggc     1440
Ile Trp Arg Gly Phe Tyr Ile Ala Gly Asp Pro Ala Leu Ala Tyr Gly
465                 470                 475                 480 tac gcc cag gac cag gaa ccc gac gca cgc ggc cgg atc cgc aac ggt     1488
Tyr Ala Gln Asp Gln Glu Pro Asp Ala Arg Gly Arg Ile Arg Asn Gly
```

```
                    485                 490                 495
gcc ctg ctg cgg gtc tat gtg ccg cgc tcg agc ctg ccg ggc ttc tac       1536
Ala Leu Leu Arg Val Tyr Val Pro Arg Ser Ser Leu Pro Gly Phe Tyr
            500                 505                 510 cgc acc agc ctg acc ctg gcc gcg ccg gag gcg gcg ggc gag gtc gaa       1584
Arg Thr Ser Leu Thr Leu Ala Ala Pro Glu Ala Ala Gly Glu Val Glu
            515                 520                 525 cgg ctg atc ggc cat ccg ctg ccg ctg cgc ctg gac gcc atc acc ggc       1632
Arg Leu Ile Gly His Pro Leu Pro Leu Arg Leu Asp Ala Ile Thr Gly
        530                 535                 540 ccc gag gag gaa ggc ggg cgc ctg gag acc att ctc ggc tgg ccg ctg       1680
Pro Glu Glu Glu Gly Gly Arg Leu Glu Thr Ile Leu Gly Trp Pro Leu
545                 550                 555                 560 gcc gag cgc acc gtg gtg att ccc tcg gcg atc ccc acc gac ccg cgc       1728
Ala Glu Arg Thr Val Val Ile Pro Ser Ala Ile Pro Thr Asp Pro Arg
                565                 570                 575 aac gtc ggc ggc gac ctc gac ccg tcc agc atc ccc gac aag gaa cag       1776
Asn Val Gly Gly Asp Leu Asp Pro Ser Ser Ile Pro Asp Lys Glu Gln
            580                 585                 590 gcg atc agc gcc ctg ccg gac tac gcc agc cag ccc ggc aaa ccg ccg       1824
Ala Ile Ser Ala Leu Pro Asp Tyr Ala Ser Gln Pro Gly Lys Pro Pro
        595                 600                 605 cgc gag gac ctg aag                                                   1839
Arg Glu Asp Leu Lys
    610

<210> SEQ ID NO 2
<211> LENGTH: 613
<212> TYPE: PRT
<213> ORGANISM: Pseudomonas aeruginosa

<400> SEQUENCE: 2

Ala Glu Glu Ala Phe Asp Leu Trp Asn Glu Cys Ala Lys Ala Cys Val
 1               5                  10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
```

-continued

```
            195                 200                 205
Leu Ala Gln Gln Arg Cys Asn Leu Asp Asp Thr Trp Glu Gly Lys Ile
210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu Gly Gly Ser Leu
                    245                 250                 255
Ala Ala Leu Thr Ala His Gln Ala Cys His Leu Pro Leu Glu Thr Phe
                260                 265                 270
Thr Arg His Arg Gln Pro Arg Gly Trp Glu Gln Leu Glu Gln Cys Gly
                275                 280                 285
Tyr Pro Val Gln Arg Leu Val Ala Leu Tyr Leu Ala Ala Arg Leu Ser
290                 295                 300
Trp Asn Gln Val Asp Gln Val Ile Arg Asn Ala Leu Ala Ser Pro Gly
305                 310                 315                 320
Ser Gly Gly Asp Leu Gly Glu Ala Ile Arg Glu Gln Pro Glu Gln Ala
                    325                 330                 335
Arg Leu Ala Leu Thr Leu Ala Ala Ala Glu Ser Glu Arg Phe Val Arg
                340                 345                 350
Gln Gly Thr Gly Asn Asp Glu Ala Gly Ala Ala Asn Ala Asp Val Val
                355                 360                 365
Ser Leu Thr Cys Pro Val Ala Ala Gly Glu Cys Ala Gly Pro Ala Asp
370                 375                 380
Ser Gly Asp Ala Leu Leu Glu Arg Asn Tyr Pro Thr Gly Ala Glu Phe
385                 390                 395                 400
Leu Gly Asp Gly Gly Asp Val Ser Phe Ser Thr Arg Gly Thr Gln Asn
                    405                 410                 415
Trp Thr Val Glu Arg Leu Leu Gln Ala His Arg Gln Leu Glu Glu Arg
                420                 425                 430
Gly Tyr Val Phe Val Gly Tyr His Gly Thr Phe Leu Glu Ala Ala Gln
                435                 440                 445
Ser Ile Val Phe Gly Gly Val Arg Ala Arg Ser Gln Asp Leu Asp Ala
450                 455                 460
Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
                    485                 490                 495
Ala Leu Leu Arg Val Tyr Val Pro Arg Ser Ser Leu Pro Gly Phe Tyr
                500                 505                 510
Arg Thr Ser Leu Thr Leu Ala Ala Pro Glu Ala Ala Gly Glu Val Glu
                515                 520                 525
Arg Leu Ile Gly His Pro Leu Pro Leu Arg Leu Asp Ala Ile Thr Gly
                530                 535                 540
Pro Glu Glu Glu Gly Gly Arg Leu Glu Thr Ile Leu Gly Trp Pro Leu
545                 550                 555                 560
Ala Glu Arg Thr Val Val Ile Pro Ser Ala Ile Pro Thr Asp Pro Arg
                    565                 570                 575
Asn Val Gly Gly Asp Leu Asp Pro Ser Ser Ile Pro Asp Lys Glu Gln
                580                 585                 590
Ala Ile Ser Ala Leu Pro Asp Tyr Ala Ser Gln Pro Gly Lys Pro Pro
                595                 600                 605
Arg Glu Asp Leu Lys
610
```

```
<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence:protease
      activatable sequence recognized by gelatinase

<400> SEQUENCE: 3

Pro Leu Gly Met Trp Ser Arg
  1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence:protease
      activatable sequence recognized by collagenase

<400> SEQUENCE: 4

Arg Pro Leu Ala Leu Trp Arg Ser
  1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence:endoplasmic
      reticulum retention sequence

<400> SEQUENCE: 5

Arg Glu Asp Leu Lys
  1               5
```